US00PP20237P3

(12) United States Plant Patent
Rasmussen

(10) Patent No.: US PP20,237 P3
(45) Date of Patent: Aug. 25, 2009

(54) ***SCHLUMBERGERA* PLANT NAMED 'CARNEVAL BRAZIL'**

(50) Latin Name: *Schlumbergera truncata*
Varietal Denomination: CARNEVAL BRAZIL

(75) Inventor: Lau Lindegaard Rasmussen, Kerteminde (DK)

(73) Assignee: Rohde's A/S, Kerteminde (DK)

( * ) Notice: Subject to any disclaimer, the term of this patent is extended or adjusted under 35 U.S.C. 154(b) by 0 days.

(21) Appl. No.: 12/082,795

(22) Filed: Apr. 14, 2008

(65) Prior Publication Data

US 2009/0070906 P1 Mar. 12, 2009

(51) Int. Cl.
*A01H 5/00* (2006.01)

(52) U.S. Cl. ..... Plt./372

(58) Field of Classification Search ..... Plt./372
See application file for complete search history.

*Primary Examiner*—June Hwu
(74) *Attorney, Agent, or Firm*—Foley & Lardner LLP

(57) ABSTRACT

A new and distinct *Schlumbergera* plant named 'Carneval Brazil', particularly characterized by large upright to vertical flowers; flowers which have petals which are red-purple (RHS N74A) and a light purple throat (RHS 75D); large quantity of flowers per plant; moderately vigorous growth rate and freely branching growth habit; and mucronate to lanceolatoid buds red-purple (RHS 71B) in color.

4 Drawing Sheets

Latin name of the genus and species of the plant claimed: *Schlumbergera truncata.*
Variety denomination: 'Carneval Brazil'.

BACKGROUND OF THE INVENTION

The present invention relates to a new and distinct cultivar of *Schlumbergera* plant, botanically known as *Schlumbergera truncata* (Haworth) Moran., commonly known as Thanksgiving Cactus, and hereinafter referred to by the cultivar name 'Carneval Brazil'.

*Schlumbergera* (formerly *Zygocactus*) of the Cactaceae family, consists of 6 known species which are epiphytic cacti and native to Brazil. Common names for *Schlumbergera* plants include: Crab Cactus for the cultivar's claw-like phylloclade margin, Thanksgiving Cactus for cultivars which bloom in November, and Christmas Cactus for cultivars which bloom in December.

The new *Schlumbergera* cultivar is a product of a planned breeding program conducted by the inventor, Lau Lindegaard Rasmussen, in Fyn, Denmark. The objective of the breeding program was to develop a new *Schlumbergera* cultivar with excellent branching habit and large, upright flowers with a unique color combination.

The new *Schlumbergera* cultivar originated from an outcrossing made by the inventor, Lau Lindegaard Rasmussen, in 2000 in Fyn, Denmark. The female or seed parent is the *Schlumbergera truncata* '8596C' (unpatented). The male or pollen parent is an unnamed, unpatented cultivar of *Schlumbergera truncata.* The new *Schlumbergera* cultivar was discovered and selected by the inventor as a single flowering plant within the progeny of the stated outcrossing in a controlled environment in 2002 in Fyn, Denmark, on the basis of its flower color and its freely branching habit. Plants of the new *Schlumbergera* are more upright and have a unique color combination of the flowers combined with healthy, glabrous green phyllocladia and excellent branching.

Asexual reproduction of the new *Schlumbergera* cultivar by phylloclade cuttings, followed by trial production batches, was first performed in January of 2003 in Fyn, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Carneval Brazil' which in combination distinguish this *Schlumbergera* as a new and distinct cultivar:

1. Large upright to vertical flowers;
2. Flowers which have petals which are red-purple (RHS N74A) and a light purple throat (RHS 75D);
3. Large quantity of flowers per plant;
4. Moderately vigorous growth rate and freely branching growth habit; and
5. Mucronate to lanceolatoid buds red-purple (RHS 71B) in color.

No plants of the female parental cultivar, *Schlumbergera truncata* '8596C', are available to provide a detailed botanical comparison to plants of the new *Schlumbergera truncata* 'Carneval Brazil'. Plants of the new *Schlumbergera truncata* 'Carneval Brazil' differ primarily from plants of the female parental cultivar, *Schlumbergera truncata* '8596C', in the following characteristics:

1. Plants of 'Carneval Brazil' have a petal color combination of red-purple which is lighter than the red-purple petal color combination of plants of '8596C';
2. Plants of 'Carneval Brazil' have a light purple throat which is darker than the light purple throat color of plants of '8596C'; and
3. Plants of 'Carneval Brazil' have broad petals, whereas plants of '8596C' have narrow petals.

Of the many commercial cultivars known to the present inventor, the most similar in comparison to the new *Schlum-*

*bergera* 'Carneval Brazil', is the *Schlumbergera truncata* 'Purple Dancer' (unpatented, disclosed in EU-CPVO No. 2004/1246) in the following characteristics:

1. Plants of 'Carneval Brazil' have a petal color combination of darker red-purple (RHS N74A) and a light purple throat (RHS 75D) whereas plants of 'Purple Dancer' have a petal color combination of lighter red-purple (RHS N74C) and a light purple throat (RHS 75D);
2. Plants of 'Carneval Brazil' have longer buds (about 4.5 to 5.0 cm in length), which are lanceolatoid to mucronate in shape, and darker red-purple (RHS 71B) in color whereas plants of 'Purple Dancer' have shorter buds (about 3.5 to 4.5 cm in length), which are obovatoid to obtuse in shape, and lighter red-purple (RHS 72D) in color;
3. Plants of 'Carneval Brazil' produce lighter green phyllocladia (mature, upper surface: RHS 137B and immature, upper surface: RHS N138B) whereas plants of 'Purple Dancer' produce darker green phyllocladia (mature, upper surface: RHS 136A and immature, upper surface: RHS 137C);
4. Plants of 'Carneval Brazil' are shorter (about 14.5 cm) than plants of 'Purple Dancer' (about 20 cm); and
5. Plants of 'Carneval Brazil' are more wider (about 22 cm in spread) than plants of 'Purple Dancer' (about 19 cm in spread).

BRIEF DESCRIPTION OF THE PHOTOGRAPHS

The accompanying photographs illustrate the overall appearance of the new *Schlumbergera* cultivar 'Carneval Brazil' showing the colors as true as is reasonably possible with colored reproductions of this type. Colors in the photographs may differ slightly from the color values cited in the detailed botanical description, which accurately describe the color of 'Carneval Brazil'.

DETAILED BOTANICAL DESCRIPTION

Figure 1:
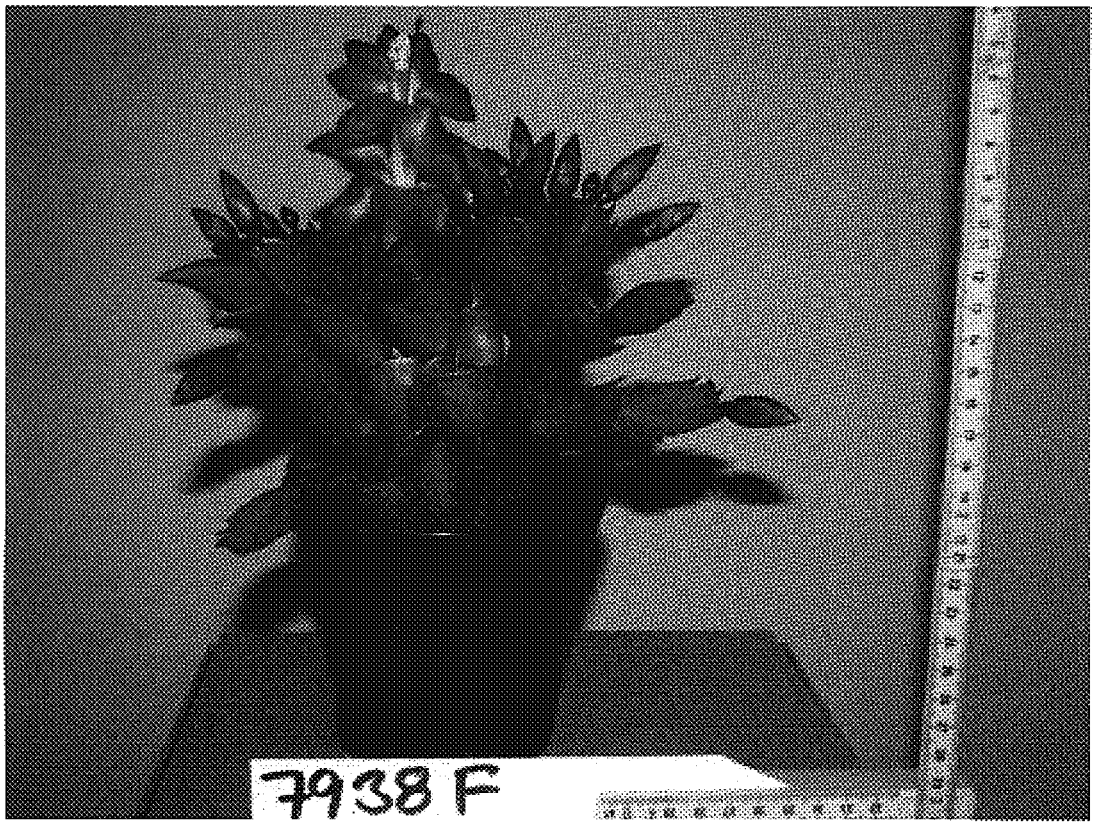
FIG. 1 shows a side perspective view of a typical flowering plant of 'Carneval Brazil' (identified by breeder's reference no. 7938F) grown in a 9.0 cm pots, at 10 to 11 months of age.
Figure 2:
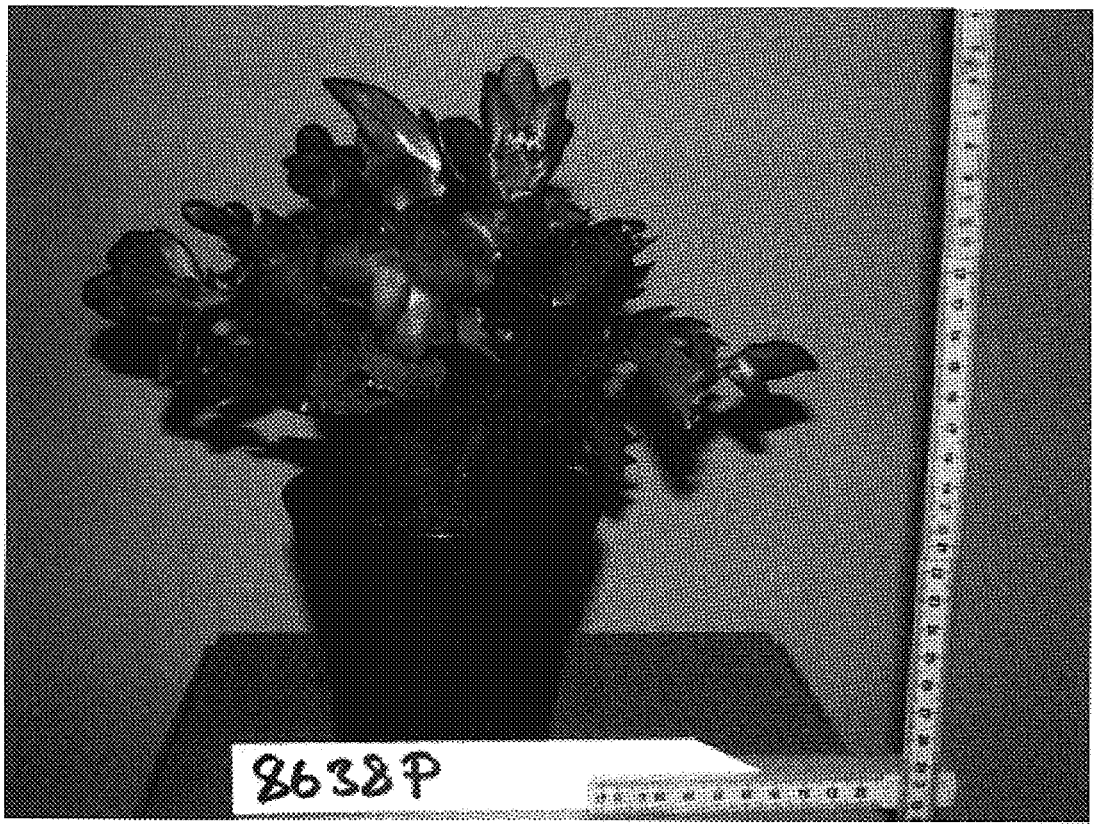
FIG. 2 shows a side perspective view of a typical flowering plant of the comparison cultivar 'Purple Dancer' (identified by breeder's reference no. 8638P) grown in a 9.0 cm pots, at 10 to 11 months of age.
Figure 3:
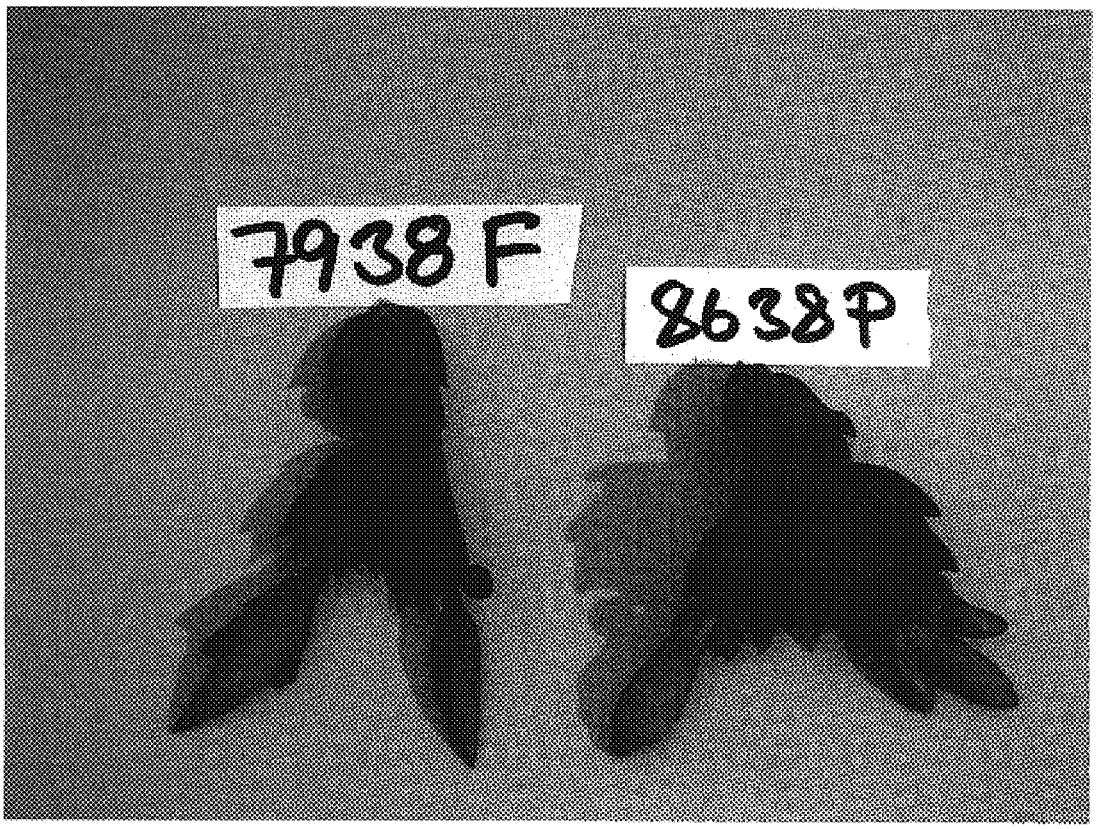
FIG. 3 shows a close-up comparison view of typical immature (not opened) flowers and phyllocladia of 'Carneval Brazil' (identified by breeder's reference no. 7938F) and typical immature (not opened) flowers and phyllocladia of 'Purple Dancer' (identified by breeder's reference no. 8638P) at 10 to 11 months of age.
Figure 4:
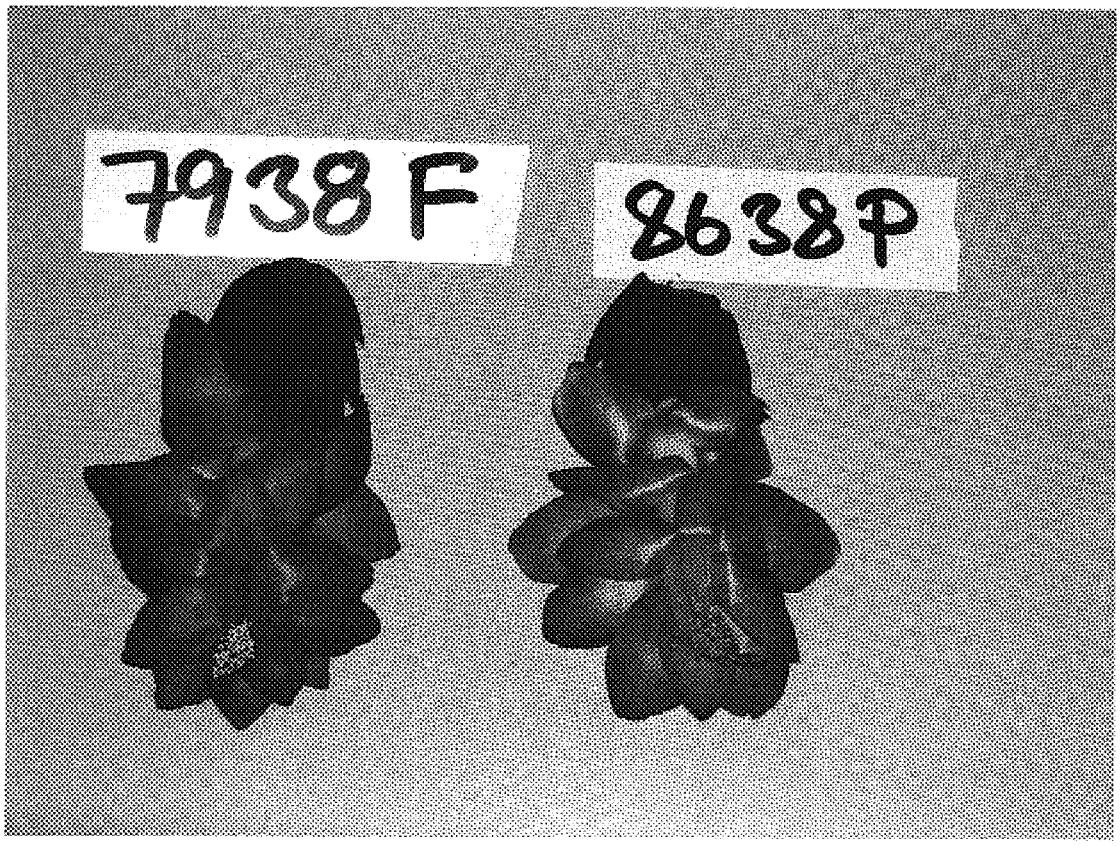
FIG. 4 shows a close-up comparison view of typical mature (fully opened) flowers and phyllocladia of 'Carneval Brazil' (identified by breeder's reference no. 7938F) and mature (fully opened) flowers and phyllocladia of 'Purple Dancer' (identified by breeder's reference no. 8638P) at 10 to 11 months of age.

The new *Schlumbergera* cultivar 'Carneval Brazil' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Carneval Brazil' as grown in a glass-covered greenhouse in Fyn, Denmark, under conditions which closely approximate those generally used in commercial practice. Plants of 'Carneval Brazil' are themophotoperiodic and will develop buds and bloom best under short day conditions (less than 12 hours of sunlight for a period of 4 weeks). Plants of 'Carneval Brazil' are grown under an average day temperature of 18° C. and an average night temperature of 16° C. Ambient light levels of +50 W m-2 were used and no growth retardants were applied when growing plants of 'Carneval Brazil'.

Color references are made to The Royal Horticultural Society Colour Chart (RHS), $4^{th}$ edition, except where general colors of ordinary significance are used. The photographs and descriptions were taken during the fall of 2007 in Fyn, Denmark, when outdoor day temperatures averaged 8° C. and outdoor night temperatures averaged 6° C. The age of the plants described is about 40 weeks after cutting.

Classification:
- *Botanical.*—*Schlumbergera truncata.*
- *Common name.*—Thanksgiving Cactus.

Parentage:
- *Female or seed parent.*—*Schlumbergera truncata* '8596C' (unpatented).
- *Male or pollen parent.*—Unnamed & unpatented *Schlumbergera truncata* cultivar.

Propagation: By single, mature phylloclade cuttings.
- *Time and temperature to initiate roots.*—In a greenhouse, about 30 days at 18° C. to 21° C.
- *Time and temperature to produce a rooted cutting.*—In a greenhouse, about 50 days at 18° C. to 21° C.
- *Rooting habit and description.*—Fine, well-branched and RHS N155D in color.

Plant:
- *Type.*—Perennial, Epiphyte.
- *Growth habit.*—Overall upright and becoming pendent as lateral branches lengthen.
- *Branching habit.*—Freely branching, with two or three new phylloclades forming at the apical of older phylloclades.
- *Vigor.*—Slow growth rate.
- *Crop time.*—After rooting, about 10 months are required to produce a finished flowering plant in an 9 cm pot.
- *Size at maturity.*—Height (soil level to top of plant, including flowers): About 14.5 cm. Spread: About 22 cm.

Stem: None, older phylloclades may turn woody with age (several years).

Lateral branches:
- *Arrangement.*—Phylloclades form at the apical end of older phylloclades to form branches.
- *Quantity.*—About 8.
- *Length.*—Primary: About 3.5 to 4.0 cm (1 phylloclade). Secondary: About 7 cm to 8 cm (2 to 3 phylloclades).
- *Width.*—About 6 cm to 7 cm.
- *Aspect.*—Upright to arching (from basal phylloclade).
- *Strength.*—Strong (from basal phylloclade).
- *Appearance.*—Glabrous and smooth.
- *Pubescence.*—None.
- *Color.*—Green, RHS N137B.

Phylloclade:
- *Arrangement.*—Single and sequential.

*Quantity per lateral branch.*—About 2 to 4.

*Length.*—About 4.2 cm to 4.5 cm.

*Width.*—About 2.8 cm to 3.5 cm.

*Thickness.*—About 6 mm to 7 mm (at center vein of phylloclade).

*Overall shape.*—Oval.

*Apex shape.*—Truncate with 2 protruding marginal teeth (about 8 mm to 9 mm in length), forming a claw-like shape.

*Base shape.*—Rounded.

*Margin.*—Serrated; about 4 teeth (about 6 mm in length).

*Texture.*—Glabrous, smooth.

*Pubescence.*—None.

*Color of upper surface.*—Immature: Green, RHS 138B. Mature: Green, RHS 137B. Margin: Green, RHS 137B.

*Color of under surface.*—Immature: Green, RHS N137B. Mature: Green, RHS 137B.

*Margin.*—Green, RHS 137B.

*Venation.*—Pattern: Costate. Color (Upper and Under Surfaces): Green, RHS 137B.

Areole: Not true areole structure; tip of phylloclade is barbellate, 10–15 short hairs or bristles.

Inflorescence description:

*Arrangement and appearance.*—Single, double or triple sessile flowers borne on apical end of phylloclades. Flowers are hose-in-hose and zygomorphic. When mature flowers are fully open, they form a right angle to the phylloclade. Flowers persistent; petals fold and wither slowly.

*Natural flowering season.*—Flowering occurs from October to December/January (Northern hemisphere), but can be changed by short day photo-treatments.

*Flowering response time.*—About 10 weeks from planting.

*Rate of flowers opening.*—About 2 per week, depending on temperature and light.

*Flowering longevity* (*dependent on temperature and light conditions*).—About 5 to 6 days.

*Fragrance.*—None.

*Quantity of flowers per lateral branch.*—About 1 to 2.

*Quantity of buds per lateral branch.*—About 6 to 8.

*Quantity of flowers and buds per plant.*—About 20 to 30.

*Flower bud.*—Length: About 4.5 cm to 5.0 cm (before anthesis). Width: About 1.3 cm to 1.6 cm (before anthesis). Shape: Lanceolatoid with mucronate tip. Color: Red-purple, RHS 71B.

*Flower.*—Type: Single. Shape: Tubular, hose-in-hose triple perianth. Aspect: Initially facing upward, later facing outward (right angle to phylloclade). Persistent or self-cleaning: Persistent, but drops after withering.

*Corolla size.*—Depth: About 6.5 cm (including ovary). Diameter: About 5.0 cm. Tube length: About 25 mm. Tube diameter: About 9 mm.

*Petals.*—Quantity: Apical Whorl: About 9. Basal whorl: About 7. Length: About 2.4 cm to 2.8 cm. Width: About 1.7 cm to 2.0 cm. Shape: Ovate. Apex: Acute. Base: Apical Whorl: Fused. Basal Whorl: Free. Margin: Entire. Appearance: Smooth. Texture: Silky (both surfaces). Color (when opening, both upper and under surfaces): Petals: Red-purple (RHS N74A). Petal Margin: Red-purple, RHS N74A. Tube: Light purple (RHS 75D). Color (when fully opened, both upper and under surfaces): Petals: Red-purple (RHS N74A). Petal Margin: Red-purple, RHS N74A. Tube: Light purple (RHS 75D). Color fading: None.

*Petaloids.*—Appearance: Same as petals. Arrangement: Free. Quantity: About 7 to 9. Length: About 3 mm to 4 mm. Width: About 5 mm. Shape: Oval. Apex: Acute. Base: Fused. Margin: Entire. Texture (both surfaces): Silky. Color (immature and mature, upper and under surfaces): Red-purple, RHS N74A.

*Sepals.*—Appearance: Same as petals. Arrangement: Free. Quantity: About 5. Length: About 20 mm. Width: About 25 mm. Shape: Ovate. Apex: Obtuse to rounded. Base: Truncate. Margin: Entire. Texture (both surfaces): Silky. Color (immature and mature, upper and under surfaces): Overall: Red-purple, RHS N74A. Margin: Red-purple, RHS N74A.

Reproductive organs:

*Androecium.*—Stamen — Quantity: About 20 to 40, polyandrous, phaenantherous, incurved. Some filaments fused to perianth tube (connate). Length: About 45 mm. Color: White, RHS 155D, translucent. Anther — Shape: Basifixed, ovoid. Length: About 1 mm. Color: Light yellow, RHS 11D. Filament — Length: About 50 mm to 60 mm. Color: White, RHS 155D, translucent. Pollen — Amount: Abundant. Color: Light yellow, RHS 11D.

*Gynoecium.*—Pistil — Quantity: 1. Shape: Slightly curved. Length: About 60 mm. Stigma — Shape: Claw-like. Color: Red-purple, RHS N74A. Style — Length: About 55 mm. Color: Red-purple, RHS N74A. Ovary — Shape: Angular. Length: About 4 to 5 mm. Width: About 5 mm. Color: Yellow-green, RHS 144A, with greyed-purple ridges, RHS 183B.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about +2° C. and to a high temperature about +40° C.

I claim:

1. A new and distinct *Schlumbergera* plant named 'Carneval Brazil', as illustrated and described herein.

* * * * *